US00PP15832P2

(12) United States Plant Patent
Evison et al.

(10) Patent No.: US PP15,832 P2
(45) Date of Patent: Jul. 5, 2005

(54) ***CLEMATIS* VARIETY 'EVIPO013'**

(50) Latin Name: *Clematis viticella*
Varietal Denomination: EVIpo013

(75) Inventors: Raymond Evison, Guernsey (GB); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/440,072

(22) Filed: May 15, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, purple flowers, and continuous summer flowering. The variety successfully propagates from softwood cuttings and is suitable for cultivation in commercial glasshouses. This new and distinct variety has shown to be uniform and stable in the resulting generations from propagation.

1 Drawing Sheet

Botanical classification: Genus: *Clematis*. Species: *viticella*.
Variety denomination: 'EVIpo013'.

SUMMARY OF THE INVENTION/DISCOVERY

The present discovery constitutes a new and distinct variety of *Clematis* which originated from uncontrolled pollination between an unknown pollen parent and the seed parent, an unnamed, non-patented, plant. The new variety, 'EVIpo013', resulted from germinating seeds of the chance pollination.

The main characteristic that distinguishes 'EVIpo013' from the seed parent variety is that the unnamed seed parent has a Violet Blue flower color. The same of 'EVIpo013' is Purple Group 79B. The objective of the cultivation of this *Clematis* variety for commercial glasshouse and nursery culture was to create a new and distinct variety with:

1. Non-clinging habit;
2. Profusion of semi-nodding purple flowers;
3. Suitability for garden situations;
4. Winter hardiness in zones 3 to 9.

These qualities required improvement in *Clematis* varieties that were in commercial cultivation and the objectives have been substantially achieved in the new variety, as evidenced by the unique combination of characteristics that are present in 'EVIpo013' which distinguish it from all other varieties of which we are aware.

The seeds, collected from the unnamed seed parent plant, were germinated and evaluations were conducted of the resulting *Clematis* plants in a controlled environment.

'EVIpo013' was selected by Raymond J. Evison and Mogens N. Olesen in their *Clematis* development program in Domarie Vineries Les Sauvagees, St. Sampsons, Guernsey, Channel Islands, United Kingdom in July, 1998.

Asexual reproduction of 'EVIpo013' by cuttings was first done by Raymond J. Evison and Mogens N. Olesen in Domarie Vineries Les Sauvagees, St. Sampsons, Guernsey, Channel Islands, United Kingdom in July 1998. This initial and subsequent propagations have demonstrated that the characteristics of 'EVIpo013' are true to type and are transmitted from one generation to the next.

BRIEF DESCRIPTION OF THE DRAWING

The accompanying color illustration show as true as is reasonably possible to obtain in color photographs of this type:

1.1 Stem and juvenile foliage;
1.2 Leaflets, upper surface;
1.3 Stem, leaves, buds closed;
1.4 Bloom, upper surface;
1.5 Bloom, lower surface.

DETAILED DESCRIPTION OF THE VARIETY

The following is a detailed description of 'EVIpo013', as observed in its growth throughout the flowering period in glasshouses at Domarie Vineries Les Sauvagees, St. Sampsons, Guernsey, Channel Islands, United Kingdom. Observed plants are 2 years of age, and were cultivated in 2 liter pots. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'Alionushka', non-patented. Chart 1 details several physical characteristics of 'EVIpo013' and the comparison variety.

CHART 1

| | 'EVIpo013' | 'Alionushka' |
|---|---|---|
| Tepal length | 40 to 50 mm. | 70 mm. |
| Bracts | Small to medium bracts on non-terminal flowers. | Large bracts on non-terminal flowers. |
| Flower color | Purple Group 79B. | Purple Group 78A. |

FLOWER AND FLOWER BUD

Blooming habit: Recurrent. The flowering months are normally, late May, June, July, August and September.

Flower bud:

*Size.*—15 to 20 mm in length.

*Bud form.*—Ovoid.

*Bud length.*—15 to 20 mm.

*Bud diameter.*—10 to 12 mm.

*Bud color.*—Purple Group 79C; Purple Group 79C at ¼ open.

*Tepals.*—Purple Group 79C.

*Peduncle.*—Surface: Smooth. Length: 120 to 180 mm. Color: Green Group 137A. Strength: Semi-nodding.

*Receptacle.*—None.

*Borne.*—Compound dichasial cymes.

Flower bloom:

*Size.*—60 to 80 mm in diameter.

*Form.*—Long companulate, with tepals slightly reflexing.

*Depth.*—30 to 50 mm.

*Color.*—Upon opening, the upper tepal surface is Purple Group 79B. Upon opening, the lower tepal is Purple Group 79B. After opening, the main color of the upper tepal surface is Purple Group 79B. After opening, the main color lower surface is Purple Group 79B. The base of the tepals is Purple Group 79B. Purple Group 79C, with a longitudinal bar of Purple Group 79B along the middle zone. As the flower ages it will fade to Purple Group 79C, with tepal margins fading to a light Purple Group 79D.

*General tonality.*—Purple.

*Variations.*—None.

*Fragrance.*—None.

*Bloom duration.*—On the plant, 7 to 10 days. As a cut flower, 2 to 4 days.

Tepals:

*Tepal count.*—Single. Average range: 4.

*Shape.*—Elliptic.

*Apex.*—Acute to apiculate.

*Base.*—Rounded.

*Length.*—40 to 50 mm, if straightened.

*Width.*—20 mm.

*Cross section.*—Strongly reflexed.

*Margin.*—Although entire the tepal margin undulates slightly 3 to 5 mm, 2 to 3 times along the length. It is difficult to quantify this undulation of the margin due to the strong recurvature of the tepal apex.

*Tepal apex.*—Narrowly acute.

*Recurvature of tip.*—Strongly recurved.

*Persistence.*—Tepals drop off cleanly.

*Arrangement.*—Tepals are arranged regularly.

Reproductive organs:

*Pollen.*—Quantity: Scant. Color: Yellow-White Group 158B.

*Anthers.*—Size: 3 to 5 mm long. Color: Yellow Group 13C. Arrangement: Regular.

*Filaments.*—Color: Yellow Group 19D.

*Styles.*—Color: Green Group 136D and Yellow Group 11D.

*Pistil.*—Quantity: 40 to 60.

*Seed.*—Quantity: Medium amount. 30 to 40 per seed head. Size: Medium. Color: Green Group 143C, ripening to Brown, Greyed-Orange Group 166C. Shape: Circular to tear shaped. Apex: Diameter 4 to 5 mm. Depth 2 mm with an elongated plumule of 15 to 25 mm in length.

PLANT

Plant form: Upright.

Plant growth: Moderately vigorous.

Height: Seasons growth attains 1.5 to 2 meters.

Spread: 0.5 M.

Hardiness: Trials to date show the variety hardy in USDA Zones 4–9.

Stems:

*Color.*—Young wood: Green Group 137C, with intonations of Purple Group 79B and Greyed-Orange Group 170A. Older wood: Greyed-Orange Group 165C.

*Internodes.*—Cross-section: Cylindrical. Length: 90 mm.

*Bark.*—Young wood: Smooth. Older wood: Smooth.

Plant foliage: Deciduous. Simple, elliptic to ovate leaves. Leaves at the base of the pedicel are occasionally trilobed and palmatisect with an average length of 90 mm and an average width of 70 mm.

*Compound leaves.*—In May, the variety occasionally produces compound leaves with the first flush of flowers, consisting of 7 leaflets arranged in pinnate form. Size: Compound leaves are normally 150 mm in length by 90 mm wide. Petiole: Length: Petioles on compound leaves are normally 40 to 50 mm. Color: Green Group 137B. Rachis: Length: Normally 100 mm. Color: Green Group 137B. Petiolule: Length: 0 to 40 mm. Color: Green Group 137B. Leaflets on Compound leaves: Length: 30 to 40 mm. Width: 15 to 20 mm. Color: Upper surface is Green Group 137A. Undersurface is Green Group 137C. Shape: Base shape is obtuse. Apex shape is acute. Margins: Entire.

*Color of mature leaves.*—Top: Medium to dark green. Green Group 137A. Bottom: Medium green. Green Group 137C.

*Simple leaves.*—Size: 80 to 100 mm (l)×50 to 60 mm (w). Stipules: Absent. Petiole: Length: 10 to 40 mm on simple leaves. Underneath: Without prickles. Color: Green Group 137B. Simple Leaf Margin: Entire. Shape: Base of simple leaf: obtuse. Apex of simple leaf: Acute. Texture: Upper side: Glabrous. Lower side: Veined. Thickness: Thin. Glossiness: Matte Finish.

Disease resistance: Subject to any disease that normally attacks the species, however the variety is more tolerant to *Botrytis* and *Clematis* Wilt than some *Clematis* known to us.

It is claimed:

1. A new and distinct variety of *Clematis* plant named 'EVIpo013', as illustrated and described herein as a distinct and novel *clematis* variety due to its abundant purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

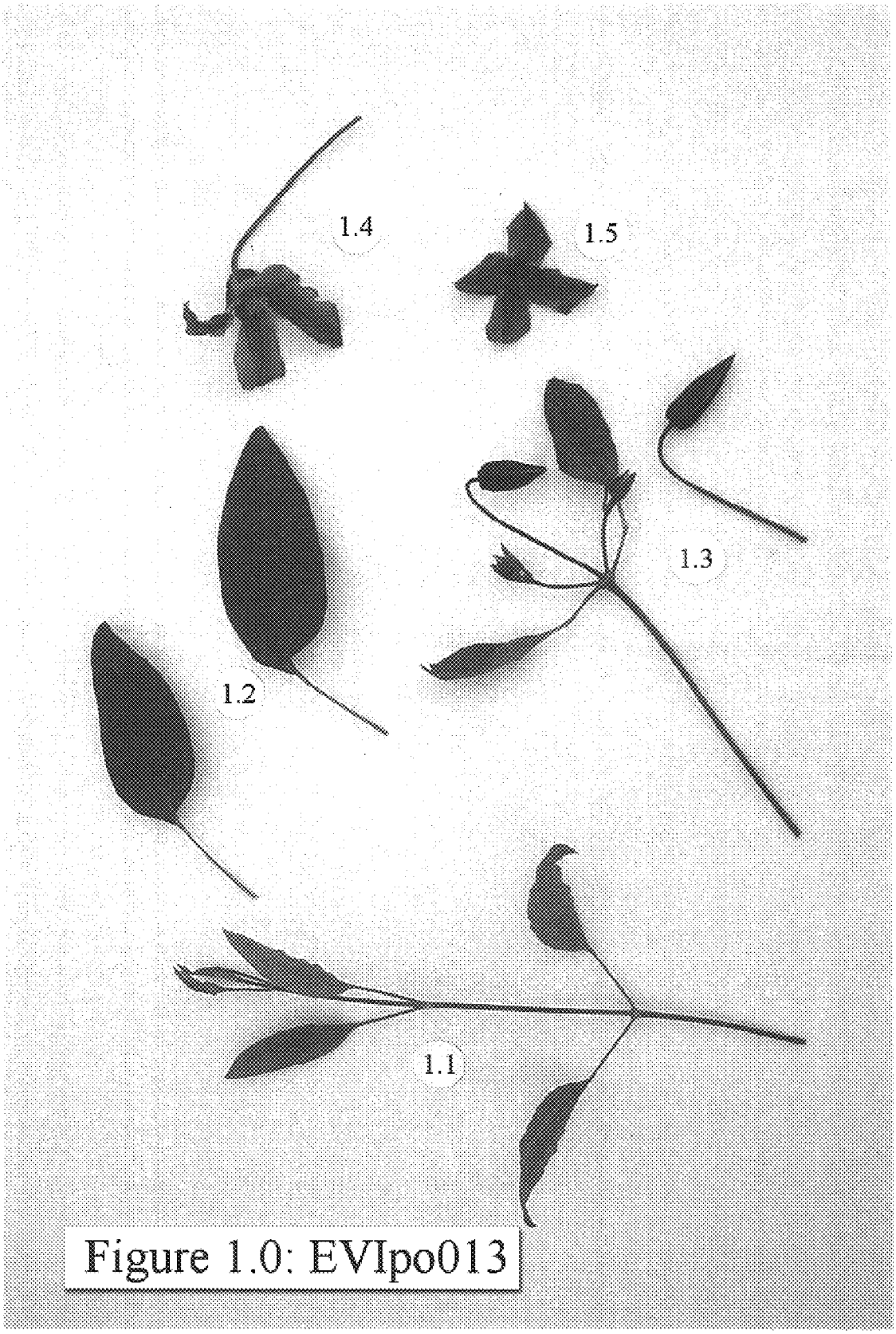
Figure 1.0: EVIpo013